(12) United States Patent
Franjic et al.

(10) Patent No.: US 11,701,013 B2
(45) Date of Patent: *Jul. 18, 2023

(54) SUCTION TOOL WITH INTEGRATED OPTICAL PROBE AND USE THEREOF (71) Applicant: SYNAPTIVE MEDICAL INC., Toronto (CA)

(72) Inventors: Kresimir Franjic, Toronto (CA); Luc Gilles Charron, Toronto (CA); Siu Wai Jacky Mak, Toronto (CA)

(73) Assignee: Synaptive Medical Inc.

( * ) Notice: Subject to any disclaimer, the term of this patent is extended or adjusted under 35 U.S.C. 154(b) by 241 days.

This patent is subject to a terminal disclaimer.

(21) Appl. No.: 17/106,618

(22) Filed: Nov. 30, 2020

(65) Prior Publication Data

US 2021/0085194 A1     Mar. 25, 2021

Related U.S. Application Data

(63) Continuation of application No. 15/573,348, filed as application No. PCT/IB2017/051096 on Feb. 24, 2017, now Pat. No. 10,945,615.

(51) Int. Cl.
*A61B 5/0215* (2006.01)
*A61F 2/958* (2013.01)
(Continued)

(52) U.S. Cl.
CPC ........ *A61B 5/0215* (2013.01); *A61B 1/00165* (2013.01); *A61B 1/3137* (2013.01); *A61B 5/0035* (2013.01); *A61B 5/0055* (2013.01); *A61B 5/0066* (2013.01); *A61B 5/0084* (2013.01); *A61B 5/065* (2013.01); *A61B 5/14503* (2013.01); *A61F 2/958* (2013.01); *A61M 1/84* (2021.05); *A61M 25/00* (2013.01); *G02B 6/0006* (2013.01); *G02B 23/2423* (2013.01); *A61B 17/320016* (2013.01); *A61M 2205/3313* (2013.01)

(58) Field of Classification Search
CPC ... A61B 5/0215; A61B 5/0035; A61B 5/0055; A61B 5/0066; A61B 5/0084; A61B 5/065; A61B 5/14503; A61B 17/320016; A61B 1/00165; A61B 1/3137; A61F 2/958; A61M 1/84; A61M 1/00; A61M 25/00; A61M 2205/3313; G02B 6/0006; G02B 23/2423

See application file for complete search history.

(56) References Cited

U.S. PATENT DOCUMENTS

2017/0014202 A1*  1/2017  Ransbury ............... A61B 18/06

\* cited by examiner

*Primary Examiner* — Peter Luong (57) ABSTRACT

A device and method is provided for a suction tool combined with an optical probe. A suction device is provided having a tip with a hollow tubular body, a plurality of optical fibers embedded in the tip and a concentric ring attached to the tip, wherein the ring end has an inner beveled reflective surface opposing the optical fibers. A method is provided for optically measuring tissue in a medical procedure comprising suctioning a tissue using a suction device, sending optical signals along optical fibers through the suction device; directing the signals from the optical fibers onto the tissue using a beveled surface; receiving optical signals from the tissue in optical fibers via the beveled reflective surface; measuring the received optical signals in a spectrometer or detector; and releasing, resecting or ablating the tissue through the suction device.

14 Claims, 11 Drawing Sheets

(51) Int. Cl.
*A61M 25/00* (2006.01)
*A61B 5/00* (2006.01)
*A61B 5/145* (2006.01)
*F21V 8/00* (2006.01)
*G02B 23/24* (2006.01)
*A61B 1/313* (2006.01)
*A61B 1/00* (2006.01)
*A61B 5/06* (2006.01)
*A61M 1/00* (2006.01)
A61B 17/32 (2006.01)

SUCTION TOOL WITH INTEGRATED
OPTICAL PROBE AND USE THEREOF

CROSS-REFERENCE TO RELATED
APPLICATION(S)

This document is a continuation application claiming the benefit of, and priority to, U.S. patent application Ser. No. 15/573,348, filed on Nov. 10, 2017, entitled "SUCTION TOOL WITH INTEGRATED OPTICAL PROBE AND USE THEREOF," a national phase entry application claiming the benefit of, and priority to, International Patent Application No. PCT/IB2017/051096, filed on Feb. 24, 2017, entitled "SUCTION TOOL WITH INTEGRATED OPTICAL PROBE AND USE THEREOF," all of which are incorporated herein by reference in their entirety.

FIELD

The present disclosure relates to image-guided medical procedures. More specifically, the present disclosure relates to an image-guided suction tool for medical procedures.

BACKGROUND

Surgical procedures have been greatly assisted by the implementation of navigation systems. Navigation systems assist in surgery by providing previously acquired imaging information, such as magnetic resonance imaging (MRI), during surgery to visualize tissue morphology and locate target areas. Navigation systems may also be used to track surgical instruments and their location within the tissue during surgery, typically incorporating information from previously acquired imaging data.

As an example, minimally invasive brain surgery may incorporate navigation systems to map a target area for surgical resection and subsequently to access the target area with surgical tools with minimal damage to healthy brain tissue. A navigation system typically includes a tracking device or object marker on a surgical tool and a detector to detect the position of the tracking device.

By tracking a surgical tool, its insertion can be guided within the tissue with minimal impact to healthy tissue and the tool can be positioned correctly to serve its purpose. The tool may be tracked by overlaying a map of its position over a previously acquired or real-time imaging of the tissue. Likewise, other navigated procedures, such as spine, ENT (ear nose throat), orthopedic, and cardiac procedures, benefit from providing surgical tools with a tracking device.

A difficulty in incorporating navigation systems in surgery is that surgical procedures which exert pressure on tissues and organs or alter their composition may deform tissue. For example, deformation of brain tissue may occur when a craniotomy is performed; and pressure on the brain is relieved, when a surgical device such as a surgical port or catheter is introduced into the brain, or when tissue is removed during surgery such as in a tumor resection. The tissue deformation may render the surgical plan based on pre-operative imaging, inaccurate and reduce the usefulness of the image-guided therapy. Thus, a need exists for real-time information regarding tissue structure, state, type, and molecular content during surgery.

SUMMARY

An aspect of the present disclosure involves addresses the foregoing challenges in providing devices and methods for an integrated suction tool and optical probe. Thus, by one broad aspect of the present disclosure, a suction device for use in a medical procedure is provided, the device comprising: an elongated tip, having a hollow tubular body, a tip proximal end and a tip distal end; a plurality of optical fibers embedded in the tip body, extending from the tip proximal end to near the tip distal end and externally accessible at the tip proximal end and near the tip distal end; and a concentric ring attached to the tip, having a first end and a second end, wherein the first end is attached to the tip distal end and the first end has an inner beveled reflective surface opposing the optical fibers near the tip distal end.

By another broad aspect of the present disclosure, a suction device for use in a medical procedure is provided, the device comprising: an elongated tip, having a hollow tubular body with a tip inner wall, a tip outer wall, a tip proximal end and a tip distal end; one or more channels in the tip outer wall extending from the tip proximal end to near the tip distal end; optical fibers within the channels; optical ports through the tip inner wall and extending from the channels near the tip distal end, for optical signal passage; and a concentric ring attached to the tip, having a first end and a second end, wherein the first end is attached to the tip distal end and the first end has an inner beveled reflective surface opposing the optical ports near the tip distal end.

By another broad aspect of the present disclosure, a method for optically measuring tissue in a medical procedure is provided, the method comprising: suctioning a tissue using a suction device; sending an optical signal along one or more optical fibers through the suction device; directing the optical signal from the optical fibers onto a tissue using a beveled surface; receiving optical signals from the tissue in optical fibers via the beveled reflective surface; measuring the received optical signals in a spectrometer or detector: and releasing or resecting the tissue through the suction device.

By a further broad aspect of the present disclosure, a method for optically measuring tissue prior to ablation in a medical procedure is provided, the method comprising: sending an optical signal along one or more optical fibers through a suction device: directing the optical signal from the optical fibers onto a tissue using a beveled surface; receiving optical signals from the tissue in optical fibers via the beveled reflective surface; measuring the optical signals in a spectrometer or detector; and ablating the tissue using optical signals along the optical fibers.

A further understanding of the functional and advantageous aspects of the present disclosure can be realized by reference to the following detailed description and drawings.

DETAILED DESCRIPTION

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

Understood is that, unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to, and explicitly incorporates, each and every specific member and combination of sub-ranges or sub-groups.

As used herein, the term "on the order of", when used in conjunction with a quantity or parameter, refers to a range spanning approximately one tenth to ten times the stated quantity or parameter.

Unless defined otherwise, all technical and scientific terms, used herein are intended to have the same meaning as commonly understood to one of ordinary skill in the art. Unless otherwise indicated, such as through context, as used herein, the following terms are intended to have the following meanings.

As used herein, the phrase "access port" refers to a cannula, conduit, sheath, port, tube, or other structure that is insertable into a subject, in order to provide access to internal tissue, organs, or other biological substances. In some embodiments, an access port may directly expose internal tissue, for example, via an opening or aperture at a distal end thereof, and/or via an opening or aperture at an intermediate location along a length thereof. In other embodiments, an access port may provide indirect access, via one or more surfaces that are transparent, or partially transparent, to one or more forms of energy or radiation, such as, but not limited to, electromagnetic waves and acoustic waves.

As used herein the phrase "intraoperative" refers to an action, process, method, event, or step that occurs, or is carried out, during at least a portion of a medical procedure. Intraoperative, as defined herein, is not limited to surgical procedures, and may refer to other types of medical procedures, such as diagnostic and therapeutic procedures.

Embodiments of the present disclosure involve suction devices that are insertable into a subject or a patient for manipulation of internal tissues, and methods of use thereof. Some embodiments of the present disclosure relate to minimally invasive medical procedures that are performed via an access port, whereby surgery, diagnostic imaging, therapy, or other medical procedures, e g, minimally invasive medical procedures, are performed based on access to internal tissue through the access port.

Several embodiments of the present disclosure seek to address the aforementioned inadequacies of existing devices and methods to support surgical procedures utilizing surgical tools.

Minimally invasive brain surgery using access ports is a recent method of performing surgery on brain tumors that were previously considered inoperable. One aspect of the present disclosure involves a system and method to assist in minimally invasive brain surgery. To address intracranial surgical concerns, specific products such as the NICO Brain-Path® port have been developed for port-based surgery.

Surgical Navigation System

The below description makes reference to the brain as an example of tissue to which the techniques herein may be applied. Understood, however, is that those techniques may also be applied to a wide variety of other tissues. Thus, when the brain is mentioned below, the brain is an example of the various tissues in connection with which the herein described systems and methods may be implemented. In particular, suction tools are widely used in surgery, thus a suction tool combined with an optical probe will be useful in virtually all types of navigated procedures. Other examples of navigated procedures wherein a suction tool/optical probe would be useful are a spine procedure, an ENT (ear-nose-throat) procedure, an orthopedic procedure, and cardiac surgery.

Figure 1:
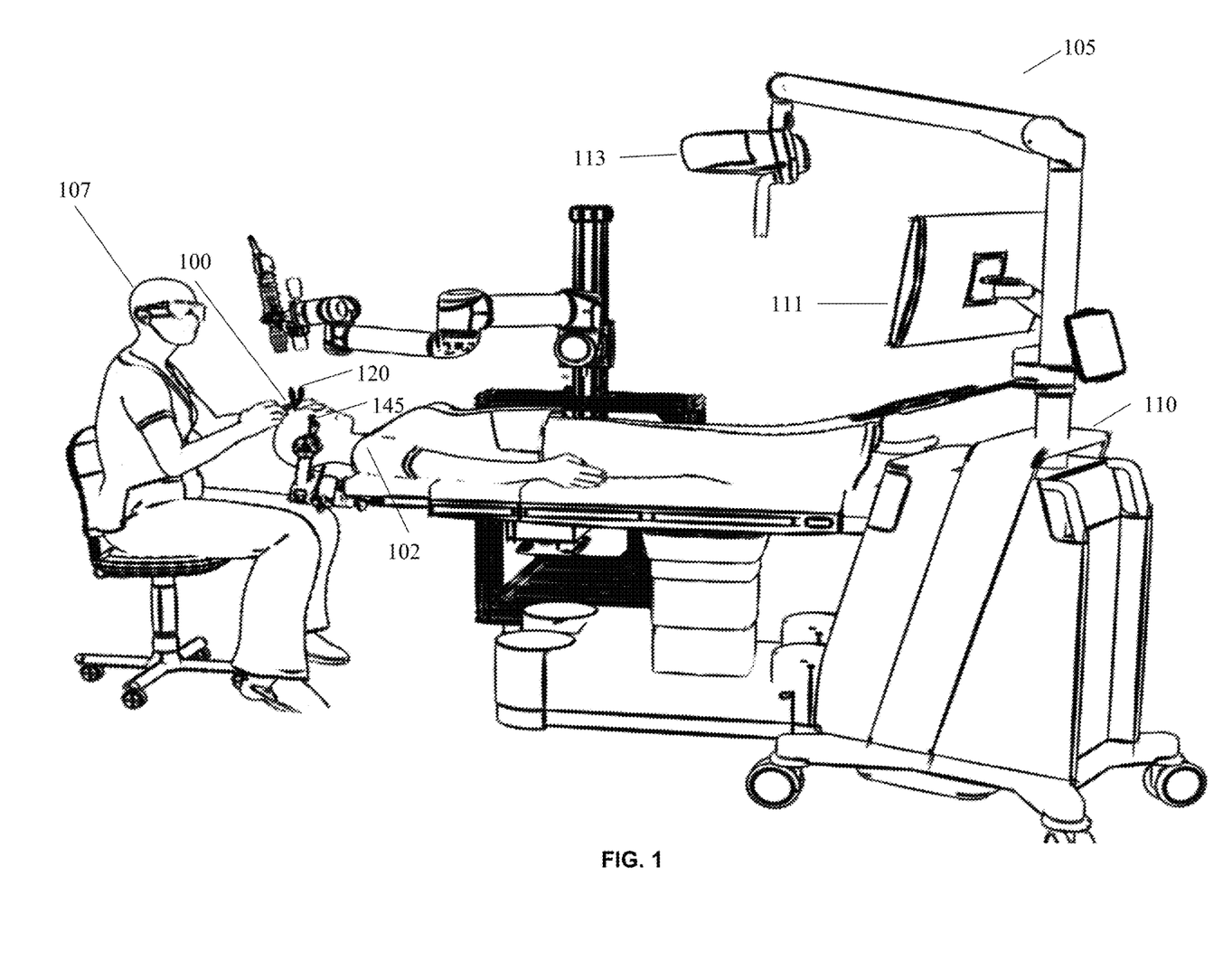
FIG. 1 is a diagram illustrating systems and equipment of an exemplary neurosurgical procedure in relation to an operating theatre, in accordance with some embodiments of the present disclosure.

Referring to FIG. 1, this diagram illustrates systems, e.g., an exemplary navigation system 105, and equipment of an exemplary neurosurgical procedure in relation to an operating theatre, in accordance with some embodiments of the present disclosure. The exemplary navigation system 105 may be used in surgery. A surgeon 107 conducts a surgery on a patient 102 in an operating room environment. The medical navigation system 105 comprises an equipment tower 110, supporting a computing device (not shown), such as a desktop computer, as well as one or more displays 111 connected to the computing device for displaying images provided by the computing device.

Still referring to FIG. 1, the equipment tower 110 also supports a tracking system 113. Tracking system 113 is generally configured to track the positions of one or more tracking markers 120 mounted on access port 100, any of the surgical tools, or any combination thereof. Such markers, also referred to as fiducial markers, may also be mounted on patient 102, for example, at various points on the head 145 of patient 102. Tracking system 113 comprises a camera, e.g., a stereo camera, and a computing device (either the same device as mentioned above or a separate device) configured to locate the fiducial markers in the images captured by the camera and determine the spatial positions of those markers within the operating theatre. The spatial positions are provided by tracking system 113 to the computing device in equipment tower 110 for subsequent use.

Still referring to FIG. 1, each tracked object generally includes three or more markers fixed at predefined locations on the object. The predefined locations, as well as the geometry of each tracked object, are configured within tracking system 113. Thus, the tracking system 113 is configured to image the operating theatre, compare the positions of any visible markers to the pre-configured geometry and marker locations, and, based on the comparison, determine which tracked objects are present in the field of view of the camera, as well as what positions those objects are currently disposed. An example of tracking system 113 is the Polaris® system available from Northern Digital, Inc.

Still referring to FIG. 1, the navigation system 105 utilizes reflective sphere markers, in combination with a stereo camera system, to determine spatial positioning and pose of the medical instruments and other objects within the operating theater. Differentiation of the types of objects and their corresponding virtual geometric volumes is determined by the specific orientation of the reflective spheres relative to one another giving each virtual object an individual identity within the navigation system 105. This differentiation allows the navigation system 105 to identify the medical instrument or other object and its corresponding virtual overlay representation. The location of the markers also provides other useful information to the tracking system 113, such as the object's central point, central axis, orientation, and other information related to the object. Alternatively, rather than reflective sphere markers, other navigation systems incorporate stickers that are reflective or that have printed patterns for machine vision recognition, active tracking, wherein either LED or RF (radio over fiber) signals are emitted to a camera or a detector for tracking, or future tracking technologies that forego tracking markers altogether.

Surgical navigation systems assist in surgery by providing pre-operative imaging information, such as magnetic resonance imaging (MRI), during surgery to visualize tissue morphology, locate target areas and track surgical instruments and their location within the tissue. However, tissues may shift between the time of the pre-operative imaging and time of the surgery. The surgical procedure, itself, produces movement and deformation of tissue. Consequently, the pre-operative images may not accurately reflect the location of the target tissue for surgery. Thus, if a surgeon guides a suction tool to a target tissue using previously acquired image data, healthy tissue may be retained by the suction tool and trauma or removal of healthy tissue may result.

The present disclosure involves tools and methods that integrate surgical tools with imaging and/or spectroscopic tools to intraoperatively provide real-time information, such as tissue structure, state, type, and molecular content. To obtain such information in a surgical area, without disturbing the workflow of surgery, integrating the optical tools into a conventional tool such as a suction device is beneficial. Furthermore, to correlate the results obtained by the optical device with those of other imaging modalities, such as MRI, PET (positron emission tomography), and CT, or the pathology results, i.e., the gold standard, it is useful to have the location tracked and recorded by a navigation system.

An important surgical tool is a suction device, which can be used for tissue retention, resection, and removal of fluids. A suction device typically includes a handle portion and tip portion. The tip portion can be any one of multiple configurations, such as different lengths, angles and diameters, and may be removable, wherein the tip portion is interchangeable to provide the most appropriate configuration for the surgical procedure. The dynamic configuration of the suction device renders the suction tip challenging to track during surgery.

Suction Tool

Figure 2:
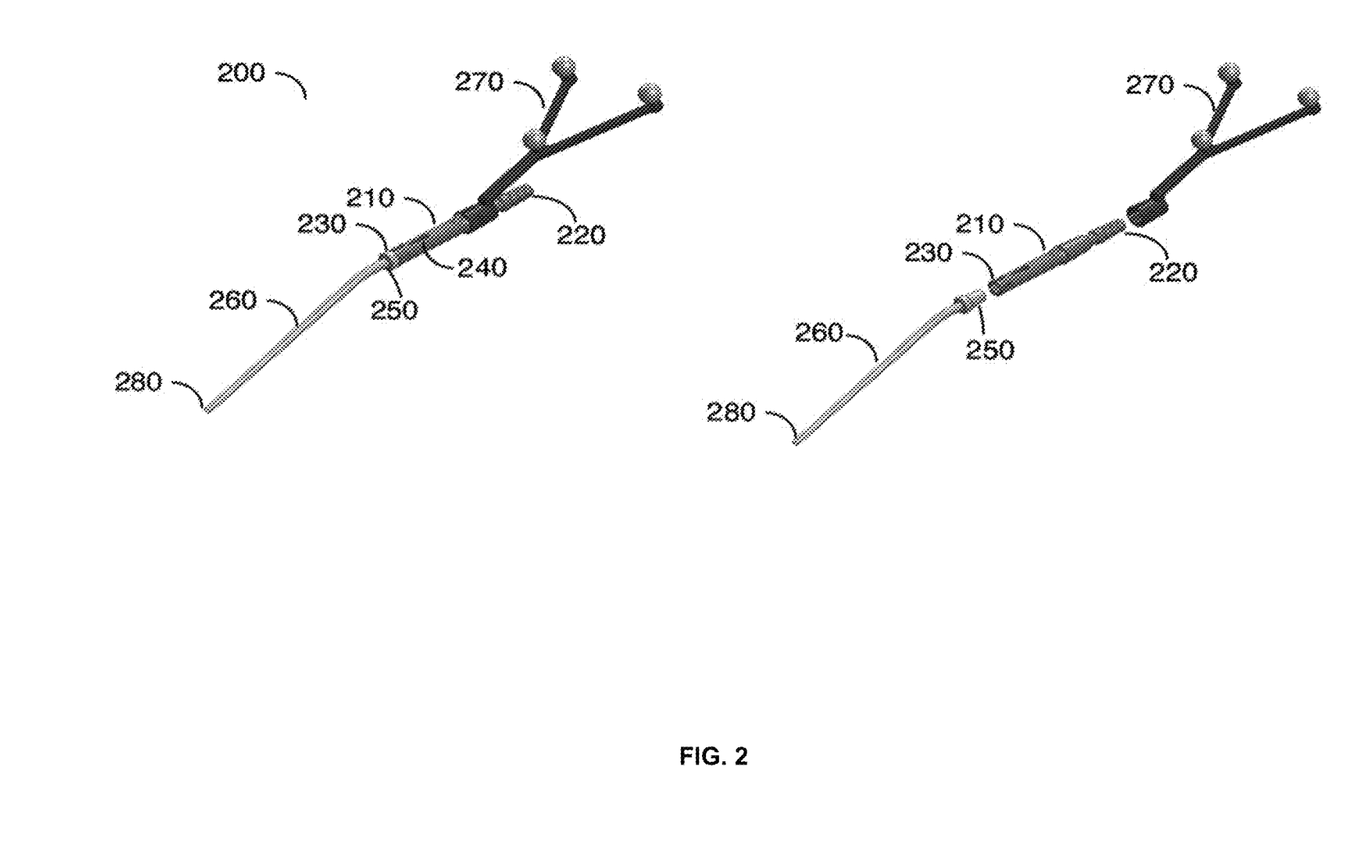
FIG. 2 is a diagram illustrating an assembled view and an exploded view of a tracked suction device, in accordance with an embodiment of the present disclosure.

Referring to FIG. 2, this diagram illustrates an example of a suction tool 200 that may be tracked during surgical procedures, in accordance with an embodiment of the present disclosure. A hollow substantially cylindrical handle 210 has a proximal end 220 and a distal end 230. The handle proximal end 220 is tapered for connection to a suction tube (not shown). The handle comprises a tapered elongated slot 240 such as a tear-shaped orifice in the wall of the handle, which is widest at the proximal end and narrowest at the distal end, for controlling the amount of suction provided by the suction tool. The handle distal end 230 is connected to a proximal end 250 of a tubular hollow tip 260. The connection could be, for example, through a snap mechanism. The snap mechanism comprises one or more outwardly protruding tabs on the tip proximal end 250 and complementary indentations on the inner surface of the hollow handle distal end 230, thus providing a key and slot method for locking connecting parts in specific rotational angles relative to the central axis. A reference tree 270 is attached to the handle 210 by sliding the reference tree 270 over the handle proximal end 220, wherein the reference tree 270 is engaged by the snap mechanism.

Still referring to FIG. 2, the handle 210 can be used to hold and manipulate the suction tool 200, such that the tip distal end 280 is directed to the tissue, e.g., for holding tissue, resecting tissue, or suctioning fluids. The tip distal end 280 is also blunted to minimize trauma to tissue while in use. The reference tree 270 provides an optical marker for tracking the position of the suction tool 200 and provides the position information to the tracking system 113. The tip 260 can be removed from the handle 210 by disengaging the snap mechanism. The tip 260 may be one of several different lengths, angles, and diameters. Thus, by removing and replacing the tip 260, the suction tool may have different configurations. Information regarding the parameters for a given tip, such as tip length, diameter, and angle, is entered and stored by the computing device of the navigation system 105, so that, for each tip 260 used with the suction tool 200, the position of the tip distal end 280 is accurately tracked.

Figure 3:
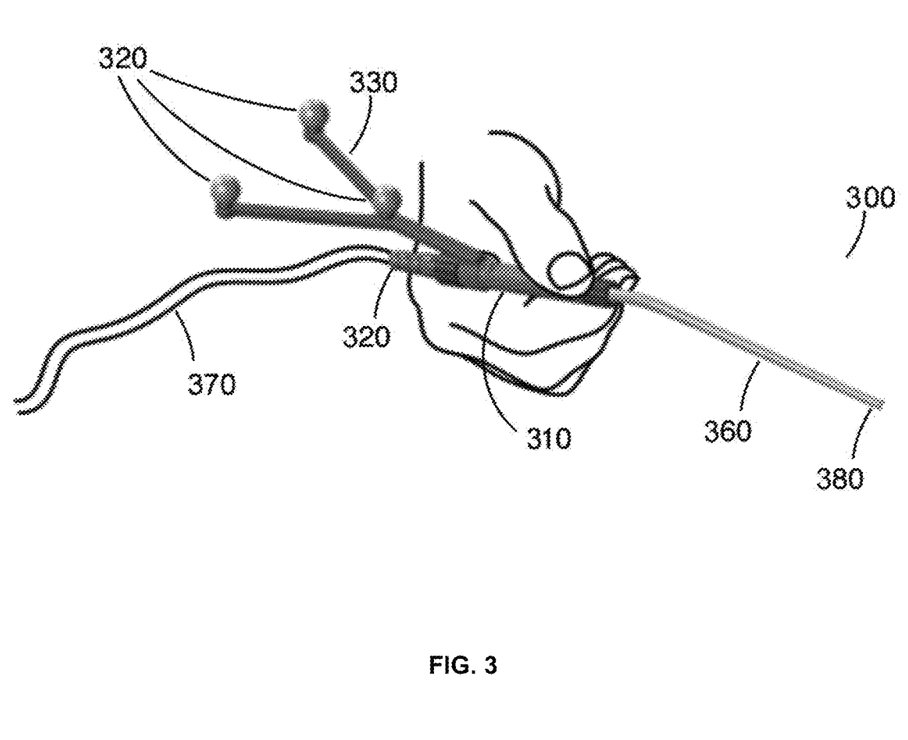
FIG. 3 is a diagram illustrating a tracked suction tool held in the hand of a user, in accordance with an embodiment of the present disclosure.

Referring to FIG. 3, this diagram illustrates a suction tool 300 is held by user, i.e., a surgeon 107, with the tracking markers 320 of the reference tree 330 providing positional information of the suction tool 300 to the tracking system 113, so the navigation system 105 is able to calculate and display the position of the suction tool tip 360 to the user, in accordance with an embodiment of the present disclosure. Suction tool 300 is connected to suction hose 370 at the tapered proximal end 320. The tapered aspect of proximal end 320 ensures for a tight and secure fit with suction hose 370.

Still referring to FIG. 3 and referring back to FIG. 2, the suction tools 200, 300 are respectively equipped with bendable hollow tips 260, 360, wherein each of the bendable hollow tips 260, 360 comprises a bend between the proximal end and distal end. The bend angle comprises a range of 60 degrees to 180 degrees, and preferably a range of 70 degrees to 170 degrees. The bend is pre-configurable or can be further bent by the user during the medical procedure. The hollow tip comprises a length in a range of 50 mm to 250 mm, and preferably a range of 100 mm to 175 mm. Further, the hollow tip comprises a diameter in a range of 3 FR to 34 FR, and preferably in a range of 5 FR to 20 FR.

Suction Tool/Optical Probe

To accommodate shifts or deformation in the tissue, assist in guiding the suction tool, and provide additional information about the tissue during surgery, e.g., tissue state, content and type, a suction tool combined with an optical probe is provided. The suction device/optical probe provides real-time imaging or spectroscopic characterization of tissue that is accessed by the suction tool/optical probe. The combined device allows tissue measurements as the suction tool is inserted into the tissue and at the site of the target tissue. The optical probe of the suction tool also provides for confirmation that the target tissue is opposed to the suction tip prior to suction and that all target tissue is removed by the suction tool.

The optical probe aspect of the suction device may be used for imaging applications, for example, optical coherence tomography (OCT) or other white light imaging techniques. Alternatively, the optical probe may be used for spectroscopy and fluorescence techniques, for example, Raman spectroscopy, a time-resolved technique, and a spectrally-resolved fluorescence technique.

Figure 4:
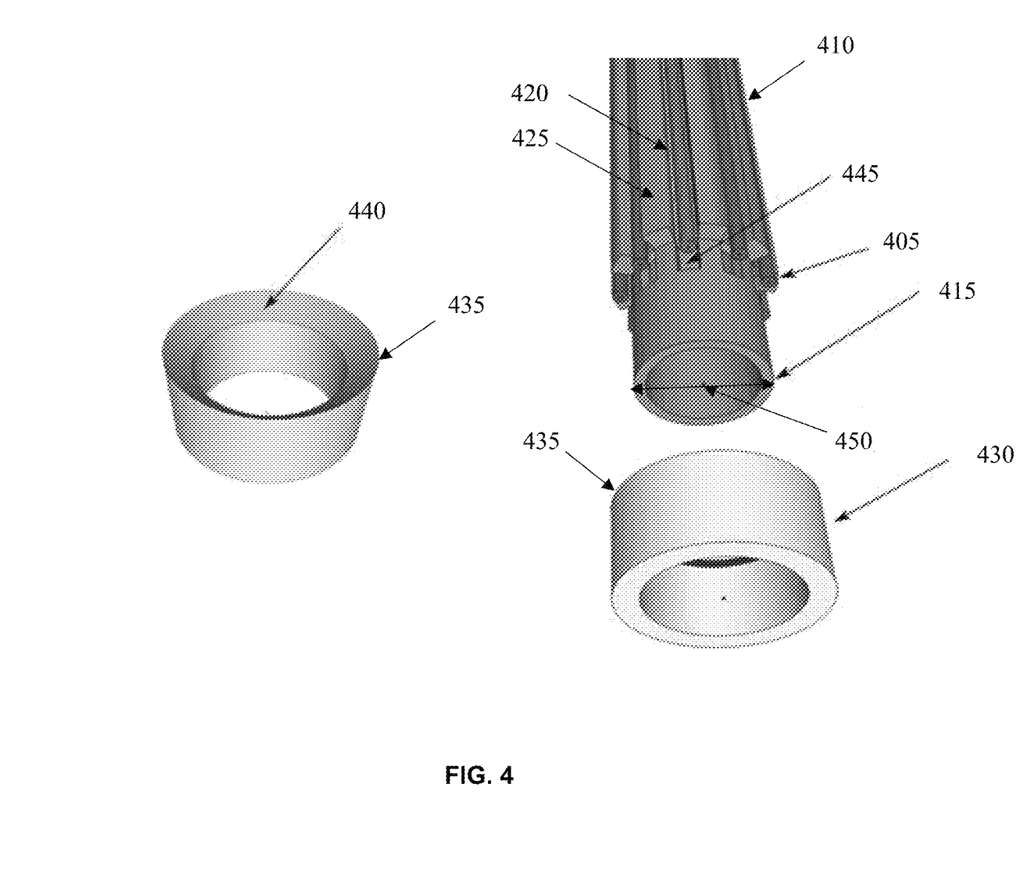
FIG. 4 is a diagram illustrating an exploded view of a suction tool tip combined with an optical probe, in accordance with an embodiment of the present disclosure.

Referring to FIG. 4, this diagram illustrates a combined suction/optical probe, in accordance with an embodiment of the present disclosure. A plurality of optical fibers 405 are embedded along the length of the suction tool tip 410 and extend close to the distal end 415 of the tip. The optical fibers 405 are embedded in longitudinal channels 420 in the outer wall 425 of the tip 410. The optical fibers 405 may also be coated, for example metal coated, to provide strength and allow flexibility if the tip 410 is bent. A concentric ring 430 is attached to the suction tip distal end 415. A proximal end 435 of the ring is beveled inwards and has a reflective surface 440, so that when positioned on the distal end of the tip 415, the beveled surface can reflect optical signals from and to the optical fibers 405.

Still referring to FIG. 4, the ring 430 comprises a molded plastic piece, such as an injection molded plastic. Possible plastic materials for the ring 430 comprise polystyrene, polycarbonate, acrylic, Zeonex®, and Ultem®. After molding the plastic ring 430, the beveled proximal end 435 can be coated with optical coatings that are highly-reflective for excitation and signal optical wavelengths to comprise a reflective surface 440. The reflective surface 440 comprises a metal coating of the beveled proximal end 435, incorporating any common metal that is first machined and then polished by diamond turning. High resolution optical coating can also be applied to increase the performance Examples of materials that may be used for reflective coatings are zinc sulfide, titanium dioxide, magnesium fluoride, and silicon dioxide.

Still referring to FIG. 4, the angle and position of the beveled proximal end 435 may vary and can be further optimized by introducing convex and concave local areas on the beveled proximal end for focusing and defocusing the optical beams. In this example, ports or openings 445 on the inside of the tip wall align with the ends of the optical fibers 405 and allow optical signals to pass from and to the optical fibers. The ports 445 may be sealed with an optically transparent resin. The outer diameter 450 of the tip is decreased for a length at the tip distal end 415, the smaller outer diameter overlapping with the distal end of the optical fibers 405, so that the ring 430 can slide onto the tip 410. In an alternate embodiment, the optical fibers 405 extend to the distal end of the tip 415 and the beveled proximal end 435 of the ring 430 abuts the distal end of the tip. In both examples, the ends of the optical fibers are externally accessible.

Figure 5:
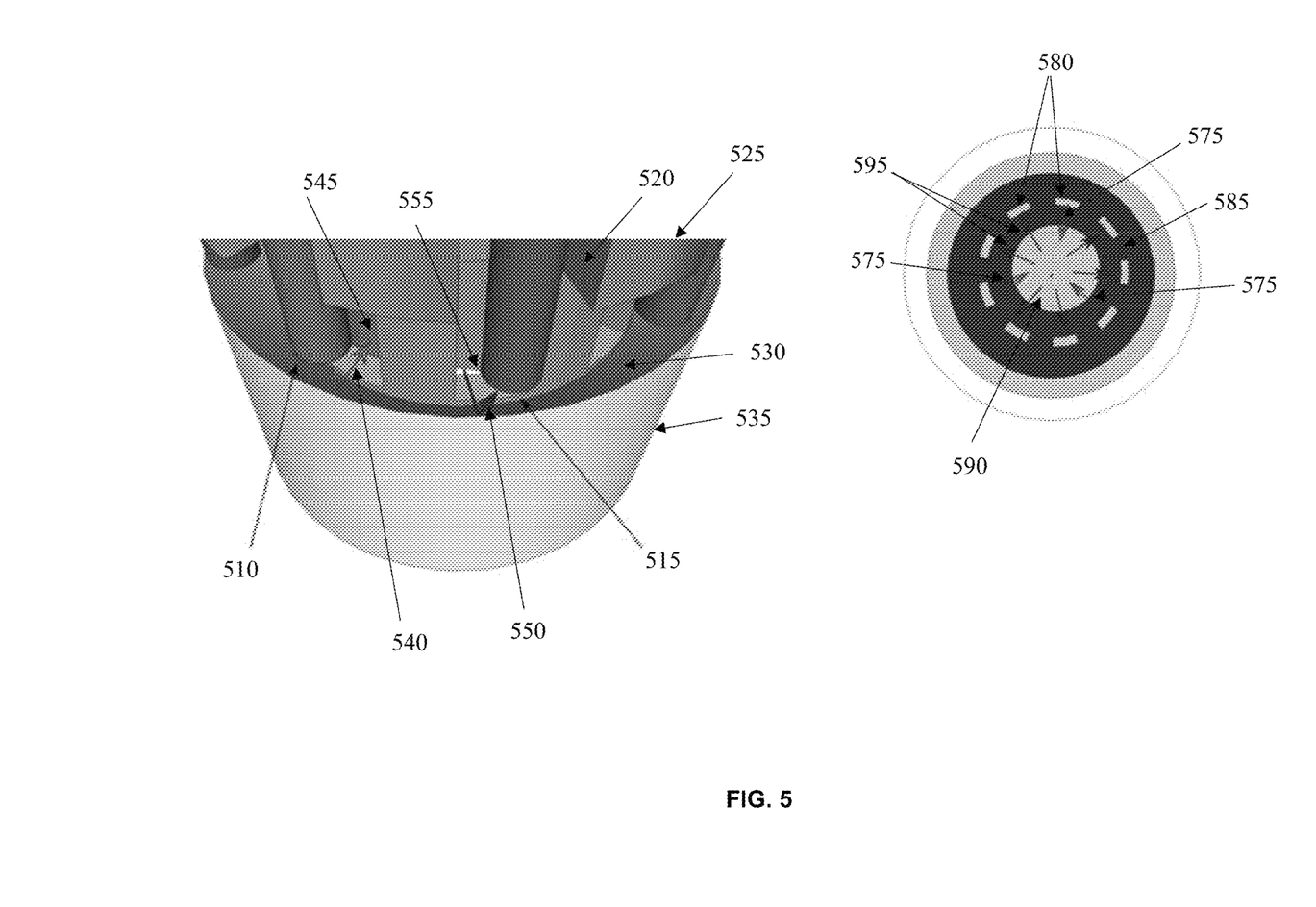
FIG. 5 is a diagram illustrating a perspective cutaway view and a bottom view of the suction tool tip/optical probe, as shown in FIG. 4, in accordance with an embodiment of the present disclosure.

Referring to FIG. 5, this diagram illustrates, in a transverse cutaway view, the relation between the signals from the optical fibers and the reflective surface of the ring proximal end. In this example, light signals refer to imaging techniques; and excitation signals refer to spectroscopic techniques. In the left hand side panel, the optical fibers 510, 515 extend through the channels 520 in the tip wall 525 to near the distal end of the tip. The reflective surface 530 of the ring 535 opposes the ends of the optical fibers 510, 515. Light or excitation signals 540 pass from an optical fiber 510 to the reflective surface 530, which reflects the light/excitation signal through the port 545 in the inner wall of the tip, toward the inner diameter of the tip. Thus, the light/excitation signals 540 are directed by the ring 535 onto the tissue at the distal end of the tip. Reflected light or excitation signals 550 travel back through a port 555 in the inner wall of the tip and are reflected by the reflective surface 530 of the ring 535 onto collection optical fibers 515. In the right hand side panel, a bottom view of the tip and optical signals is shown. Light/excitation signals 575 pass through ports 580 in the inside tip wall 585 onto the beveled surface 590 of the ring and reflective signals 595 are reflected from the beveled surface through ports 580 in the inside tip wall 585 to be collected by a collection optical fiber.

Figure 6:
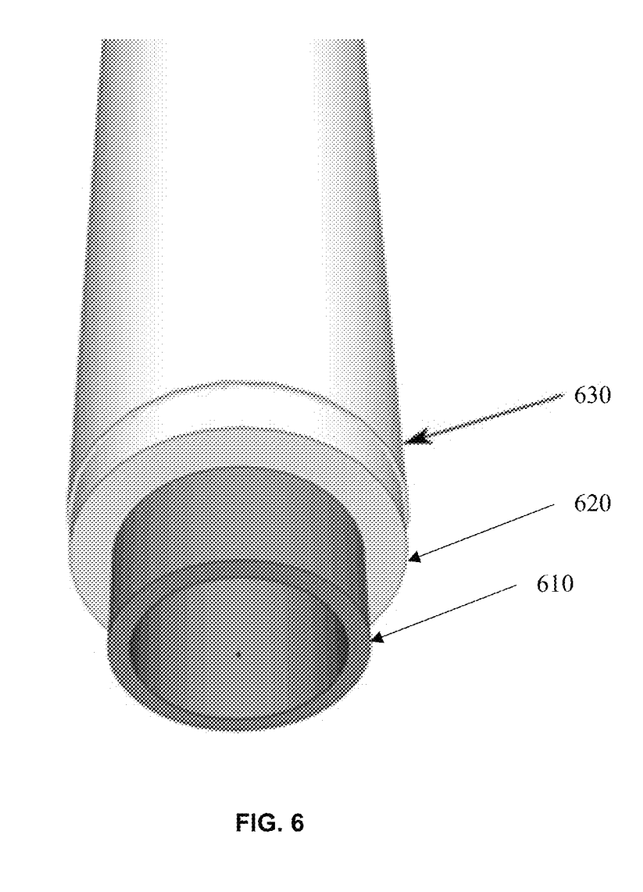
FIG. 6 is a diagram illustrating a sealed suction tool tip/optical probe, in accordance with an embodiment of the present disclosure.

Referring to FIG. 6, this diagram illustrates the components of the suction/optical probe, including the tip wall 610 and the ring 620 are sealed, in accordance with an embodiment of the present disclosure. The components may be epoxied and sealed with a thin sleeve 630, such as a thermal shrink tubing, to exclude fluids from entering during surgery and prevent tissue and fluids from lodging near the optical fibers and blocking optical signals.

Figure 7:
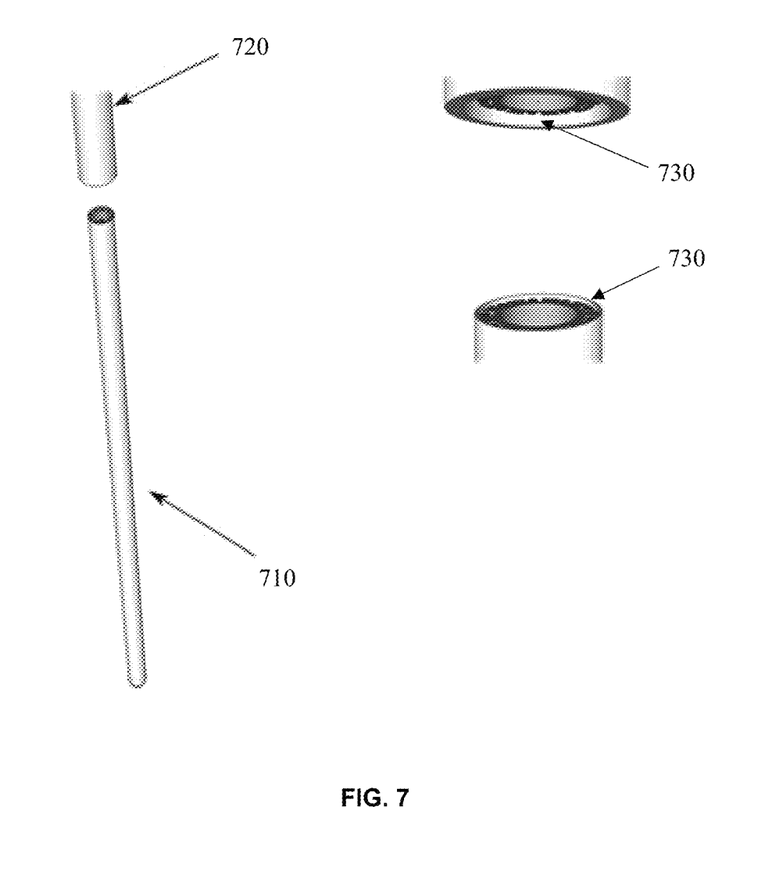
FIG. 7 is a diagram illustrating an exploded perspective view and a close-up cutaway perspective view of an attachment of a suction tool tip/optical probe to a suction tool handle, in accordance with an embodiment of the present disclosure.

Referring to FIG. 7, this diagram illustrates the suction tool tip 710 attached to an elongated tubular handle, having a centrally longitudinal passage, in accordance with an embodiment of the present disclosure. The tip 710 is reversibly attached to the suction tool handle 720, thereby allowing consumable tips to be used with a permanent suction handle. Examples of reversible attachment mechanisms for lockably attaching the tip 710 to the handle 720 are a snap mechanism or a threaded ring mechanism. The tip 710 and handle 720 are attached such that optical fibers in the tip are aligned with complementary optical fibers in the handle at the attachment point 730, for example, using asymmetric tabs and complementary recesses.

Figure 8:
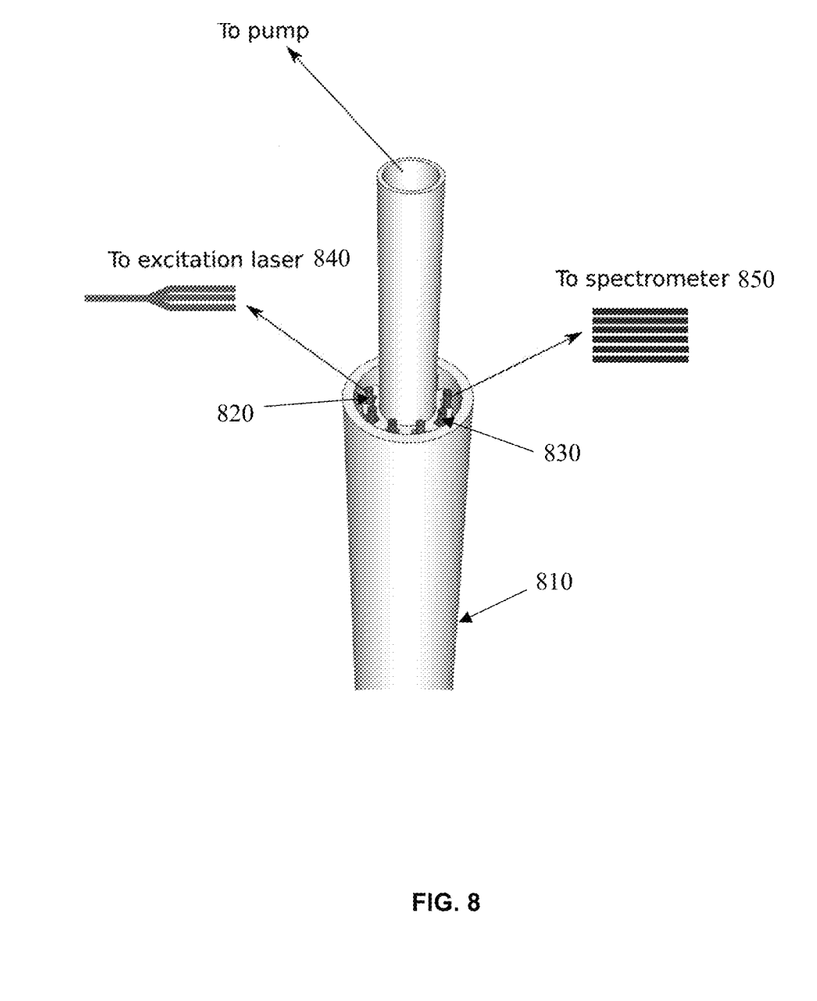
FIG. 8 is a diagram illustrating a cutaway view of a suction tool handle combined with an optical probe, in accordance with an embodiment of the present disclosure.

Referring to FIG. 8, this diagram illustrates the suction tool handle 810 houses optical fibers 820, 830 for light/excitation signals and collection signals, in accordance with an embodiment of the present disclosure. The handle optical fibers 820, 830 are complementary to and align with the optical fibers in the suction tool tip. A hollow longitudinal passage in the handle connects to a pump or other vacuum source. In an embodiment, wherein the optical probe incorporates spectroscopic techniques, preferably such as Raman spectroscopy, a time-resolved technique, and a spectrally-resolved fluorescence technique, excitation optical fibers 820 from the handle are connected to an excitation light source 840 while collection optical fibers 830 are connected to a spectrometer or detector 850. Collection signals may be analyzed using a computer device and data from the signals may be presented on a computer display and correlated with images, including images obtained prior to the surgical procedure and images of the position of the suction tool based on tracking markers.

Still referring to FIG. 8, in an embodiment, wherein the optical probe incorporates imaging techniques, such as Optical Coherence Tomography, any one of the fibers in optical fibers 820 and 830 can be coupled to an OCT module instead of an excitation laser or a spectrometer. The OCT module will direct laser light to the tissue through an internal interferometer to the fiber 820 or 830. Light scattered from the laser light will be collected through the same fiber 820 or 830 back to the interferometer to generate light interference with an internal reflected light which is then directed to a detector for detection. Noted is that the detection of the scatter light for OCT could also be a spectrometer or a photodetector. A real time varying one dimensional (A-scan) can be obtained using this configuration. Further information regarding OCT system and methods is provided in International application No. PCT/IB2017/050226 entitled "SYSTEM AND METHOD FOR PROVIDING SURGICAL GUIDANCE BASED ON POLARIZATION-SENSITIVE OPTICAL COHERENCE TOMOGRAPHY" which is incorporated by reference herein.

Figure 9:
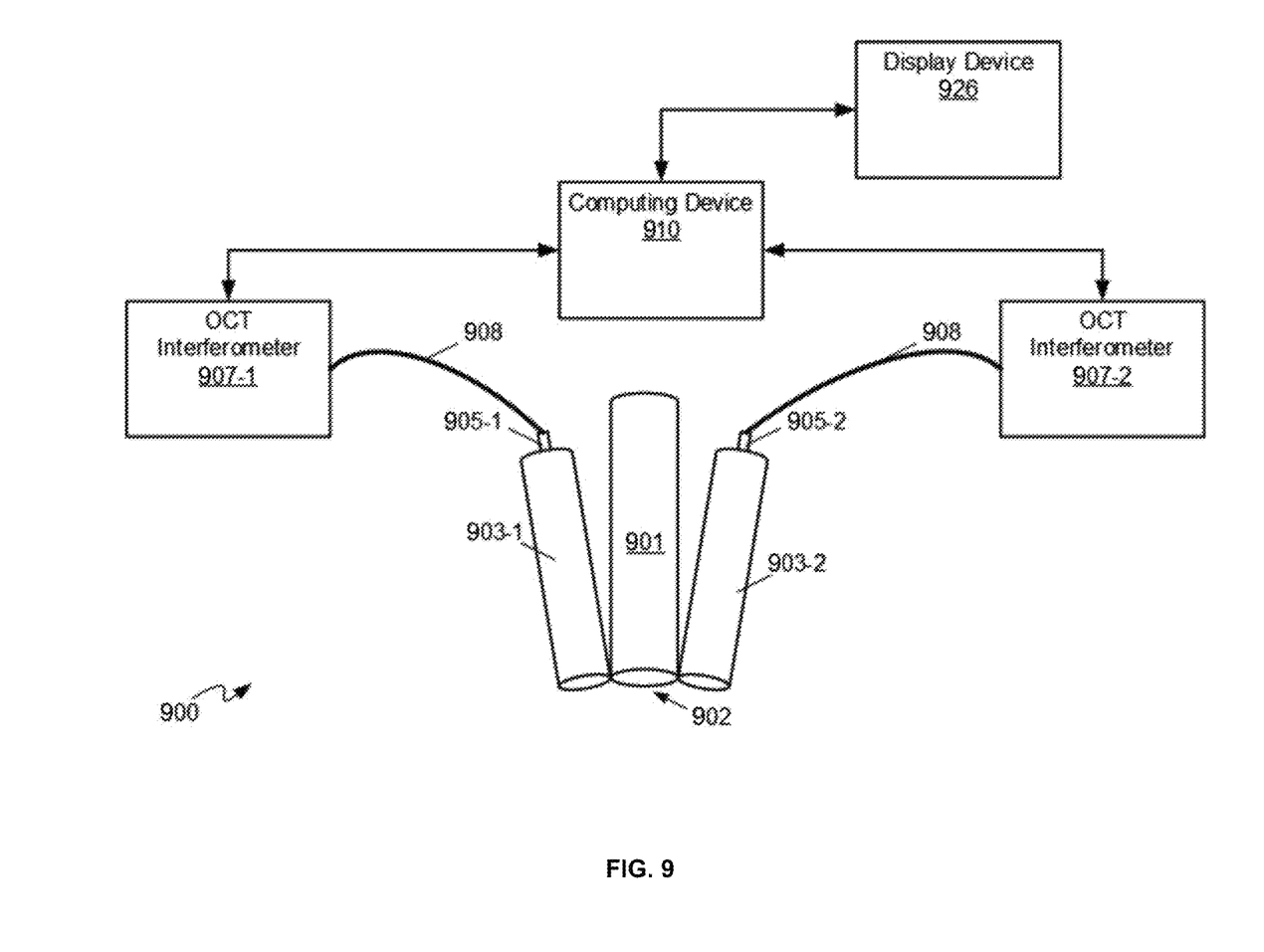
FIG. 9 is a diagram illustrating an imaging probe of the device, as shown in FIG. 4, in accordance with an embodiment of the present disclosure.

Referring to FIG. 9, this diagram illustrates the optical probe 903-1, 903-2 (hereafter collectively referred to as "optical probe 903") aspect of the suction device 901 incorporating imaging techniques, such as optical coherence tomography (OCT), the optical fibers connect through an optical fiber 908 to an interferometer 907-1, 907-2 (hereafter collectively referred to as "an interferometer 907"), in accordance with an alternate embodiment of the present disclosure. Light, such as laser light, from the interferometer 907 passes through the optical fibers and is scanned across tissue by the optical probe 903, and the optical probe collects light scattered from the tissue. Hence, in this embodiment, the optical probe 903 comprises a scanning component including but not limited to a microelectromechanical (MEMS) and a photoacoustic scanner, and a focusing element including micro-lens, gradient-index (GRIN) lenses and ball lenses. The scanning component is configured to scan OCT light across a line and/or an area of tissue to obtain a two or three dimensional OCT image respectively.

Still referring to FIG. 9, each OCT interferometer comprises: a light source, one or more optical couplers and/or beam splitters, and a reference arm having at least a reference mirror; and at least one detector. The light source may be directed to an optical coupler and/or beam splitter which splits the OCT light, e.g., laser light, into a reference arm and a sample arm. In the reference arm, the OCT light is directed to a mirror that sets a reference imaging distance from optical coupler and/or beam splitter. The OCT light then reflects back to the optical coupler and/or beam splitter. In the sample arm, the optical coupler and/or beam splitter may direct the OCT light to a respective optical probe which, in turn, directs the OCT light to tissue to generate light scattering from the tissue. The reflected light from tissue is received through the same OCT probe which directs the light back to the optical coupler in the OCT interferometer. The reflected light from tissue and the reference mirror then interferes and forms a fringe pattern which creates an A-scan OCT signal through Fourier transformation. As an OCT scan is performed, the OCT interferometer produces an OCT output, which is received by a computing device 910 and combined at a display device 926 in an OCT image.

Figure 10:
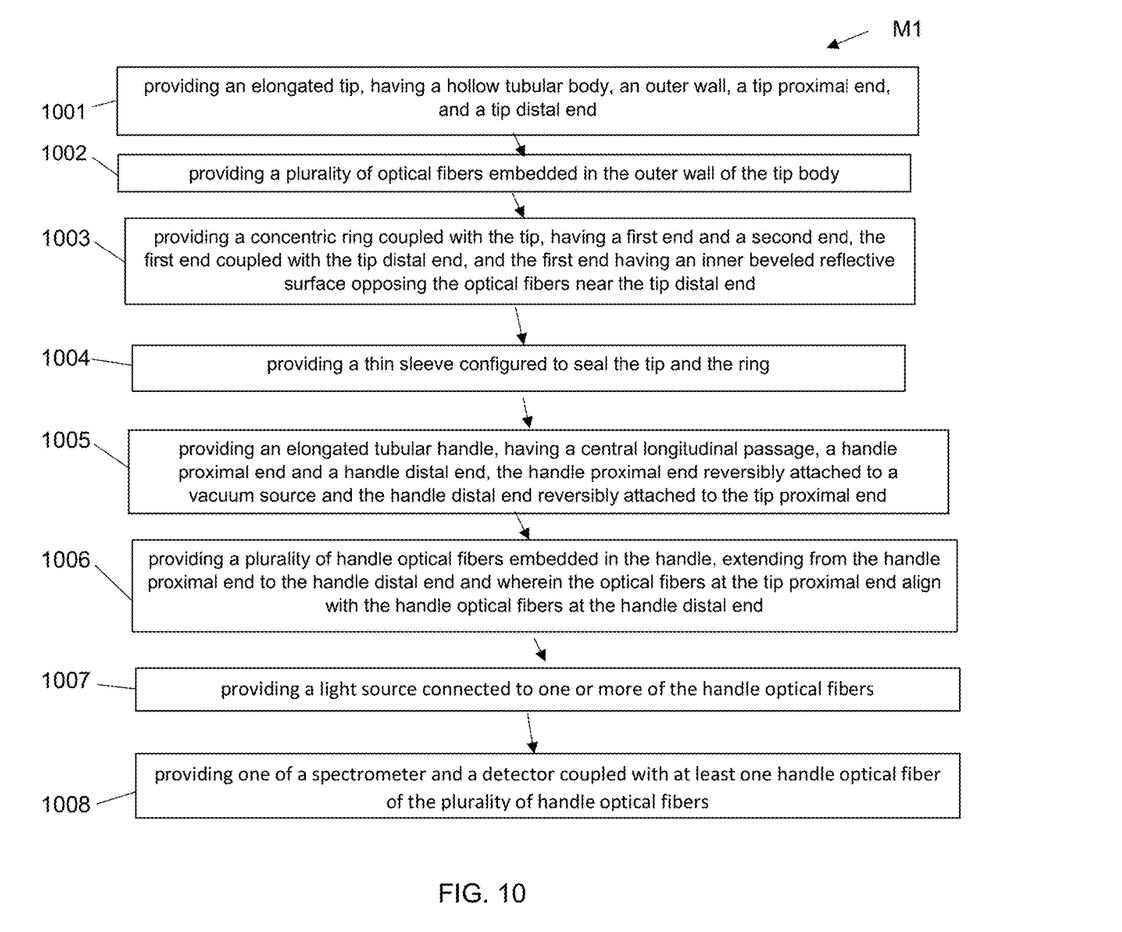
FIG. 10 is a flow diagram illustrating a method of providing a suction device for use in a medical procedure, in accordance with an embodiment of the present disclosure.

Referring to FIG. 10, this flow diagram illustrates a method M1 of providing a suction device for use in a medical procedure, in accordance with an embodiment of the present disclosure. The method M1 comprises: providing an elongated tip, having a hollow tubular body, an outer wall, a tip proximal end, and a tip distal end, as indicated by block 1001; providing a plurality of optical fibers embedded in the outer wall of the tip body, as indicated by block 1002; and providing a concentric ring coupled with the tip, having a first end and a second end, the first end coupled with the tip distal end, and the first end having an inner beveled reflective surface opposing the optical fibers near the tip distal end, as indicated by block 1003.

Still referring to FIG. 10, in the method M1, providing an elongated tip comprises providing the tip outer wall with at least one channel in the extending from the tip proximal end to near the tip distal end; providing the plurality of optical fibers comprises providing the plurality of optical fibers as embedded within the at least one channel; and providing a plurality of optical ports comprises providing the plurality of optical ports as disposed through the tip inner wall, as extended from the at least one channel near the tip distal end, and as configured for transmitting an optical signal. In the method M1, providing the plurality of optical fibers comprises providing the plurality of optical fibers as extending from the tip proximal end to near the tip distal end; and providing the plurality of optical fibers comprises providing the plurality of optical fibers as externally accessible at the tip proximal end and near the tip distal end.

Still referring to FIG. 10, the method M1 further comprises at least one of: providing a thin sleeve configured to seal the tip and the ring, as indicated by block 1004; providing an elongated tubular handle, having a central longitudinal passage, a handle proximal end and a handle distal end, the handle proximal end reversibly attached to a vacuum source and the handle distal end reversibly attached to the tip proximal end, as indicated by block 1005; providing a plurality of handle optical fibers embedded in the handle, extending from the handle proximal end to the handle distal end and wherein the optical fibers at the tip proximal end align with the handle optical fibers at the handle distal end, as indicated by block 1006; providing a light source connected to one or more of the handle optical fibers, as indicated by block 1007; and providing one of a spectrometer and a detector coupled with at least one handle optical fiber of the plurality of handle optical fibers, as indicated by block 1008.

Still referring to FIG. 10, in the method M1, at least one of: providing the elongated tubular handle comprises providing the handle as coupled with the tip by one of a snap mechanism and a threaded ring, providing the plurality of optical ports comprises providing the plurality of optical ports as sealed with an optically transparent resin; providing the concentric ring comprises providing the inner beveled reflective surface angle in a range of 0 degrees to 89 degrees; providing the elongated tip comprises providing the tip as bendable, providing the plurality of optical fibers comprises providing each optical fiber as at least one of: a single mode fiber, a multi-mode fiber; a photonic crystal fiber, a polarization-maintaining fiber, and a metal coated fiber, providing the concentric ring comprises providing the concentric ring as a molded plastic feature configured to slidably couple with the tip distal end.

Figure 11:
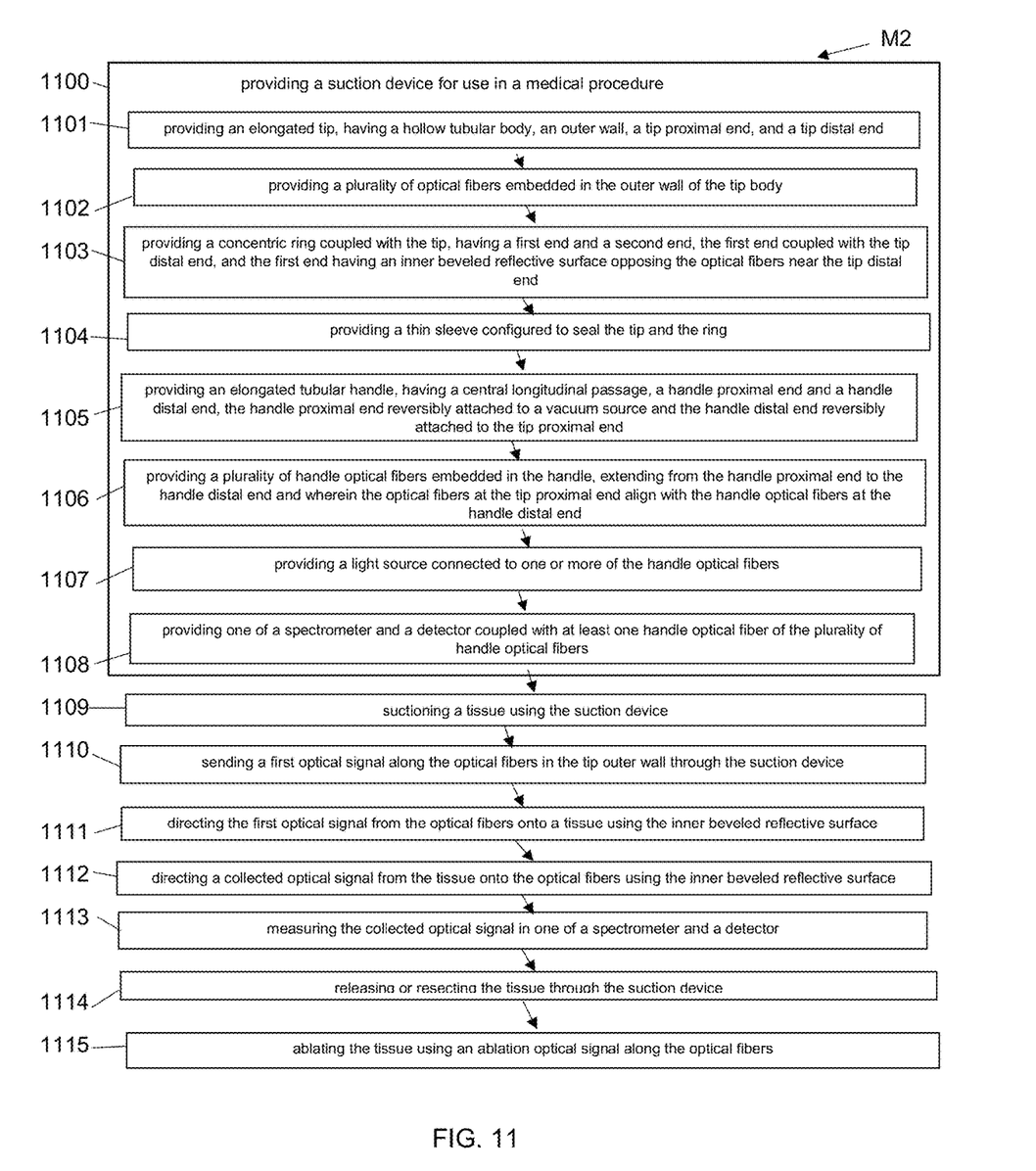
FIG. 11 is a flow diagram illustrating a method of optically measuring tissue in a medical procedure by way of a suction device, in accordance with an embodiment of the present disclosure.

Referring to FIG. 11, this flow diagram illustrates a method M2 of optically measuring tissue in a medical procedure by way of a suction device, in accordance with an embodiment of the present disclosure. The method M2 comprises: providing a suction device for use in a medical procedure, as indicated by block 1100, providing the suction device comprising: providing an elongated tip, having a hollow tubular body, an outer wall, a tip proximal end, and a tip distal end, as indicated by block 1101; providing a plurality of optical fibers embedded in the outer wall of the tip body, as indicated by block 1102; and providing a concentric ring coupled with the tip, having a first end and a second end, the first end coupled with the tip distal end, and the first end having an inner beveled reflective surface opposing the optical fibers near the tip distal end, as indicated by block 1103.

Still referring to FIG. 11, the method M2 further comprises at least one of: suctioning a tissue using the suction device, as indicated by block 1109; sending a first optical signal along the optical fibers in the tip outer wall through the suction device, as indicated by block 1110; directing the first optical signal from the optical fibers onto a tissue using the inner beveled reflective surface, as indicated by block 1111; directing a collected optical signal from the tissue onto the optical fibers using the inner beveled reflective surface, as indicated by block 1112; measuring the collected optical signal in one of a spectrometer and a detector, as indicated by block 1113; releasing or resecting the tissue through the suction device, as indicated by block 1114; and ablating the tissue using an ablation optical signal along the optical fibers, as indicated by block 1115.

Still referring to FIG. 11, the method M2 further comprises at least one of: providing a thin sleeve configured to seal the tip and the ring as indicated by block 1104; providing an elongated tubular handle, having a central longitudinal passage, a handle proximal end and a handle distal end, the handle proximal end reversibly attached to a vacuum source and the handle distal end reversibly attached to the tip proximal end, as indicated by block 1105; providing a plurality of handle optical fibers embedded in the handle, extending from the handle proximal end to the handle distal end and wherein the optical fibers at the tip proximal end align with the handle optical fibers at the handle distal end, as indicated by block 1106; a light source connected to one or more of the handle optical fibers, as indicated by block 1107; and providing one of a spectrometer and a detector coupled with at least one handle optical fiber of the plurality of handle optical fibers, as indicated by block 1108.

Still referring to FIG. 11, in the method M2, at least one of: providing an elongated tip comprises providing the tip outer wall with at least one channel in the extending from the tip proximal end to near the tip distal end; providing the plurality of optical fibers comprises providing the plurality of optical fibers as embedded within the at least one channel; providing a plurality of optical ports comprises providing the plurality of optical ports as disposed through the tip inner wall, as extended from the at least one channel near the tip distal end, and as configured for transmitting an optical signal; providing the plurality of optical fibers comprises providing the plurality of optical fibers as extending from the tip proximal end to near the tip distal end, and providing the plurality of optical fibers comprises providing the plurality of optical fibers as externally accessible at the tip proximal end and near the tip distal end, and The suction/optical probe may be used intraoperatively to provide guided insertion and use of a suction tool. The suction tool tip is attached to the handle, using a locking mechanism for reversibly attaching the tip and handle. The attachment mechanism also provides alignment of optical fibers embedded in the tip and handle. The handle is attached to a suction or vacuum pump to provide suction. The tip is guided through a tissue, while optical signals travel from a light source, through the optical fibers in the handle and corresponding optical fibers in the tip, and from the distal end of the optical fibers onto the reflective surface of the ring, which directs the optical signal forward and inward to the tissue ahead of the suction/optical tool. Optical signals from the tissue are collected back on the reflective surface of the ring, and onto the collection optical fibers in the tip, through the collection optical fibers in the handle, to a spectrometer or detector. The collection optical signals are read and analyzed to provide imaging or spectroscopy of the tissue in front of the probe as the probe is inserted toward the target tissue. Using the information from the optical signals to identify whether the measured tissue is the target tissue, the tissue may be suctioned, resected or ablated using the suction tool/optical probe.

The specific embodiments described above have been shown by way of example, and understood is that these embodiments may be susceptible to various modifications and alternative forms. Further understood is that the claims are not intended to be limited to the particular forms disclosed, but rather to cover all modifications, equivalents, and alternatives falling within the spirit and scope of the present disclosure.

What is claimed:

1. A suction device for use in a medical procedure, the device comprising:
 an elongated tip, having a hollow tubular body, an outer wall, a tip proximal end, and a tip distal end;
 a plurality of optical fibers embedded in the outer wall of the tip body; and
 a concentric ring coupled with the tip, having a first end and a second end, the first end coupled with the tip distal end, and the first end having an inner beveled reflective surface opposing the optical fibers near the tip distal end.

2. The device of claim 1,
 wherein the tip outer wall comprises at least one channel in the extending from the tip proximal end to near the tip distal end,
 wherein the plurality of optical fibers are embedded within the at least one channel, and
 wherein a plurality of optical ports are disposed through the tip inner wall, extend from the at least one channel near the tip distal end, and are configured for transmitting an optical signal.

3. The device of claim 2,
 wherein the plurality of optical fibers extend from the tip proximal end to near the tip distal end, and wherein the plurality of optical fibers externally accessible at the tip proximal end and near the tip distal end, and further comprising:

an elongated tubular handle, having a central longitudinal passage, a handle proximal end and a handle distal end, the handle proximal end reversibly attached to a vacuum source and the handle distal end reversibly attached to the tip proximal end;

a plurality of handle optical fibers embedded in the handle, extending from the handle proximal end to the handle distal end and wherein the optical fibers at the tip proximal end align with the handle optical fibers at the handle distal end;

a light source connected to one or more of the handle optical fibers; and one of a spectrometer and a detector coupled to the plurality of handle optical fibers.

4. The device of claim 3, wherein the handle is coupled with the tip by one of a snap mechanism and a threaded ring.

5. The device of claim 2, wherein the plurality of optical ports is sealed with an optically transparent resin.

6. The device of claim 1, wherein the inner beveled reflective surface angle comprises a range of 0 degrees to 89 degrees.

7. The device of claim 1, wherein the tip is bendable.

8. The device of claim 1, wherein each optical fiber of the plurality of optical fibers comprises at least one of: a single mode fiber, a multi-mode fiber; a photonic crystal fiber, a polarization-maintaining fiber, and a metal coated fiber.

9. The device of claim 1, wherein the concentric ring comprises a molded plastic feature configured to slidably couple with the tip distal end.

10. The device of claim 1, further comprising a thin sleeve configured to seal the tip and the ring.

11. A method of optically measuring tissue in a medical procedure by way of a suction device, the method comprising:

providing a suction device for use in a medical procedure, providing the suction device comprising:

providing an elongated tip, having a hollow tubular body, an outer wall, a tip proximal end, and a tip distal end;

providing a plurality of optical fibers embedded in the outer wall of the tip body; and providing a concentric ring coupled with the tip, having a first end and a second end, the first end coupled with the tip distal end, and the first end having an inner beveled reflective surface opposing the optical fibers near the tip distal end;

suctioning a tissue using the suction device;

sending a first optical signal along the optical fibers in the tip outer wall through the suction device;

directing the first optical signal from the optical fibers onto a tissue using the inner beveled reflective surface;

directing a collected optical signal from the tissue onto the optical fibers using the inner beveled reflective surface;

measuring the collected optical signal in a spectrometer or a detector; and releasing or resecting the tissue through the suction device.

12. The method of claim 11, wherein providing an elongated tip comprises providing the tip outer wall with at least one channel in the extending from the tip proximal end to near the tip distal end, wherein providing the plurality of optical fibers comprises providing the plurality of optical fibers as embedded within the at least one channel, and wherein providing a plurality of optical ports comprises providing the plurality of optical ports as disposed through the tip inner wall, as extended from the at least one channel near the tip distal end, and as configured for transmitting an optical signal.

13. The method of claim 12, wherein providing the plurality of optical fibers comprises providing the plurality of optical fibers as extending from the tip proximal end to near the tip distal end, and wherein providing the plurality of optical fibers comprises providing the plurality of optical fibers as externally accessible at the tip proximal end and near the tip distal end, and further comprising:

providing an elongated tubular handle, having a central longitudinal passage, a handle proximal end and a handle distal end, the handle proximal end reversibly attached to a vacuum source and the handle distal end reversibly attached to the tip proximal end;

providing a plurality of handle optical fibers embedded in the handle, extending from the handle proximal end to the handle distal end and wherein the optical fibers at the tip proximal end align with the handle optical fibers at the handle distal end; a light source connected to one or more of the handle optical fibers; and providing one of a spectrometer and a detector coupled with at least one handle optical fiber of the plurality of handle optical fibers.

14. The method of claim 11, further comprising ablating the tissue using an ablation optical signal along the optical fibers.

* * * * *